(12) United States Patent
Stamos

(10) Patent No.: US 7,347,810 B2
(45) Date of Patent: Mar. 25, 2008

(54) DEVICE FOR DRAINING THE CORONARY SINUS

(76) Inventor: Thomas A. Stamos, 1441 Schoettler Rd., Chesterfield, MO (US) 63017

( * ) Notice: Subject to any disclaimer, the term of this patent is extended or adjusted under 35 U.S.C. 154(b) by 567 days.

(21) Appl. No.: 10/956,973

(22) Filed: Oct. 1, 2004

(65) Prior Publication Data
US 2006/0074378 A1   Apr. 6, 2006

(51) Int. Cl.
A61M 1/10   (2006.01)
(52) U.S. Cl. .......................................... 600/17; 600/16
(58) Field of Classification Search ................. 600/16, 600/17; 623/3.1, 3.26, 3.28
See application file for complete search history.

(56) References Cited

U.S. PATENT DOCUMENTS

| | | | |
|---|---|---|---|
| 3,995,617 A | 12/1976 | Watkins et al. ............. 128/1 D |
| 4,240,409 A | 12/1980 | Robinson et al. ........... 128/1 D |
| 4,332,259 A * | 6/1982 | McCorkle, Jr. ............. 607/123 |
| 4,697,574 A | 10/1987 | Karcher et al. ............. 128/1 D |
| 4,705,507 A | 11/1987 | Boyles ........................ 604/101 |
| 4,771,765 A | 9/1988 | Choy et al. ................... 600/18 |
| 4,861,330 A | 8/1989 | Voss ............................. 600/18 |
| 4,902,272 A | 2/1990 | Milder et al. ................. 600/18 |
| 4,934,996 A * | 6/1990 | Mohl et al. ................... 600/17 |
| 5,176,619 A | 1/1993 | Segalowitz ................... 600/18 |
| 5,376,114 A | 12/1994 | Jarvik ............................ 623/3 |
| 5,425,708 A * | 6/1995 | Nasu ....................... 604/102.03 |
| 5,449,342 A | 9/1995 | Hirose et al. .................. 604/4 |
| 5,609,629 A | 3/1997 | Fearnot et al. ................. 623/1 |
| 6,117,077 A * | 9/2000 | Del Mar et al. ............. 600/301 |
| 6,139,517 A | 10/2000 | Macoviak et al. ............. 604/8 |
| 6,217,541 B1 | 4/2001 | Yu ................................. 604/9 |
| 6,254,563 B1 | 7/2001 | Macoviak et al. ............. 604/8 |
| 6,471,633 B1 | 10/2002 | Freed .......................... 600/16 |
| 6,508,777 B1 | 1/2003 | Macoviak et al. ......... 604/4.01 |
| 2001/0027287 A1* | 10/2001 | Shmulewitz et al. .......... 604/7 |
| 2003/0138350 A1 | 7/2003 | Macoviak et al. |
| 2003/0187322 A1 | 10/2003 | Siess |

* cited by examiner

Primary Examiner—George R. Evanisko
Assistant Examiner—Amanda Patton
(74) Attorney, Agent, or Firm—Polster, Lieder, Woodruff & Lucchesi, L.C.

(57) ABSTRACT

A device for draining a coronary sinus comprises a first catheter having a distal end, a proximal end, and a passage there through, the distal end adapted to be placed in a coronary sinus, a second catheter having a distal end, a proximal end, and a passage there through, the distal end adapted to be placed in a right side of a heart, and a control system for receiving signals indicative of a coronary sinus needing to be drained of blood, the control system comprising a pump for pumping blood from a coronary sinus through the first catheter to the second catheter into a right side of a heart.

7 Claims, 5 Drawing Sheets

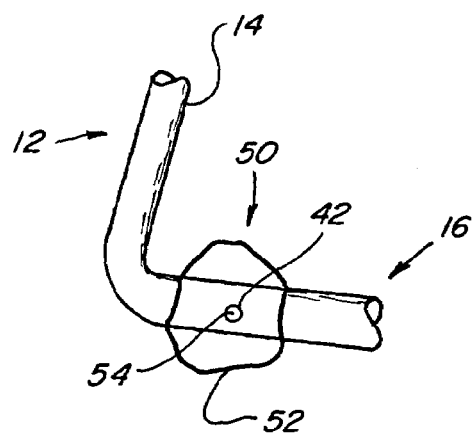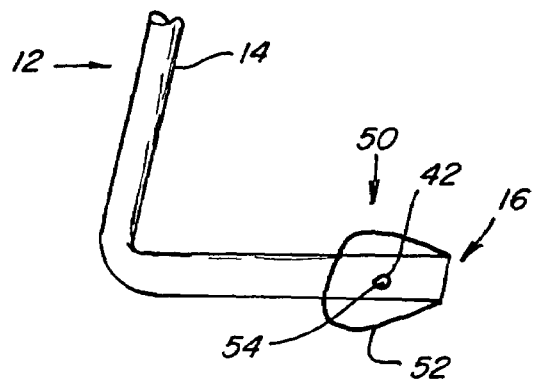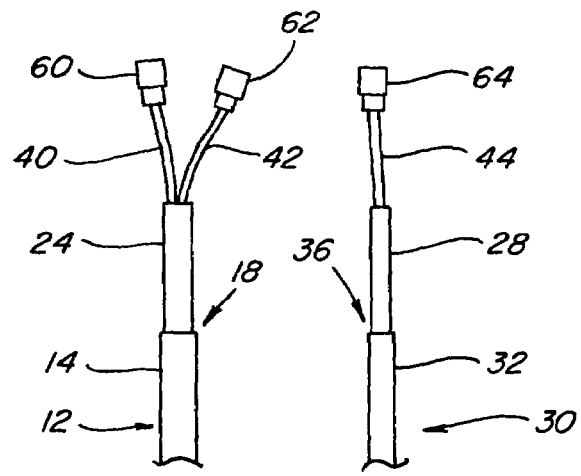

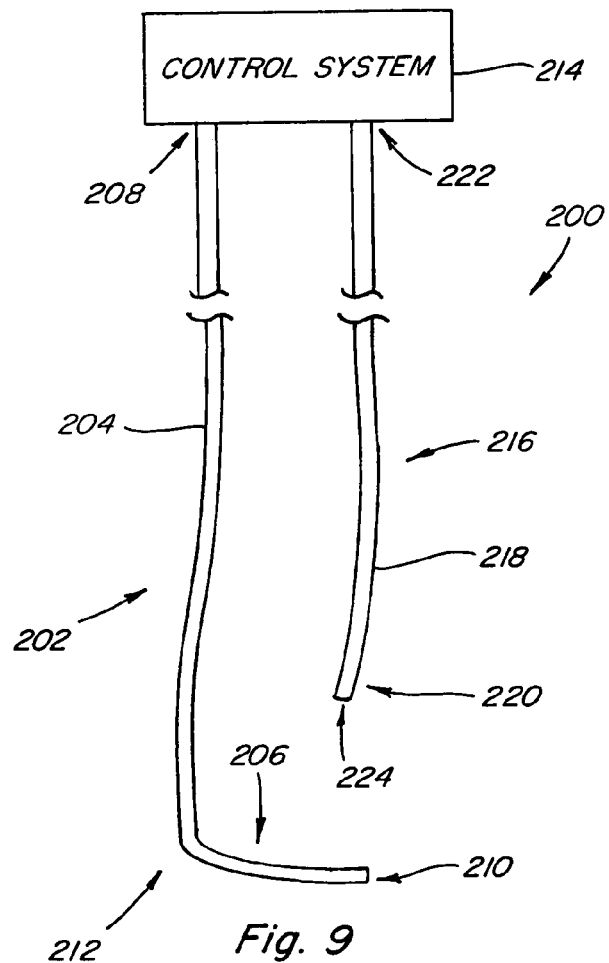
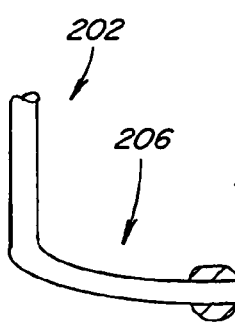
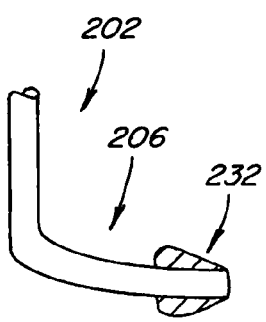
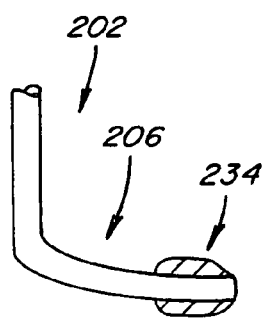
Fig. 9
Fig. 10
Fig. 11
Fig. 12

DEVICE FOR DRAINING THE CORONARY SINUS

BACKGROUND OF THE INVENTION

This invention relates to a cardiac assist device or a device for assisting the pumping of a heart, and more particularly, to a catheter having a pump for draining the coronary sinus of the heart. Specifically, the coronary sinus pump assists in the venous drainage of the heart that should occur during both the diastolic and systolic function of the heart.

The heart is divided into a left side and a right side. The left side of the heart performs the function of pumping oxygenated blood from the lungs to the rest of the body. The right side of the heart receives deoxygenated blood returning from the body and then sends this blood to the lungs to be supplied with oxygen. Each side of the heart has an upper chamber, referred to as an atrium, and a lower chamber, called a ventricle. The atrial chambers accumulate blood and supply blood to the ventricular chambers that then pump blood to the body. The ventricular chambers operate in a pumping fashion by expanding and drawing blood in from the atriums, then contracting and forcing blood out to the body. Inlet and outlet check valves within the chambers operate to insure that blood flows in the proper directions. The right atrium and the right ventricle are separated by a tricuspid valve. The right ventricle pumps blood out through a pulmonary valve into pulmonary arteries that then carry blood away from the heart to the lungs. The left atrium and the left ventricle are separated by a mitral valve. The left ventricle pumps blood out through an aortic valve into the aorta that then carries oxygen-rich blood from the heart to the body.

Deoxygenated blood returns from the body to the right atrium of the heart by means of the superior vena cava and the inferior vena cava. Diastole is the resting phase in the heart cycle. Systole is the active or pumping phase of the heart. During the heart's diastole or expansion, blood is drawn through the tricuspid valve into the right ventricle. During the heart's systole or contraction, blood is forced from the right ventricle into the pulmonary artery. Oxygenated blood returns from the lungs via pulmonary veins and enters into the left atrium. During the heart's systole, blood is forced out of the left ventricle, through the aortic valve, and into the aorta to be carried off to all parts of the body including the heart. If the heart does not properly rest or relax, this can subsequently hinder the systolic phase or the pumping phase of the heart. This improper heart relaxation will compromise the ability of the heart to pump blood to the rest of the body. If this occurs, then the heart will fail.

The blood supply that serves the heart muscle with oxygenated blood originates from two openings called coronary ostia in the aorta near the aortic valve. Blood flows from the coronary ostia through the coronary arteries and branches off into many tiny capillaries to provide oxygenated blood to all areas of the heart muscle. Most of the blood entering the coronary arteries drains through veins into the coronary sinus vein that in turn drains into the right atrium. However, there are times when the heart is not able to drain blood in the coronary sinus back into the right atrium. This may be due to congestive heart failure or muscle damage caused by a heart attack. During periods of time in which the heart is not capable of moving some or all of the blood from the coronary sinus to the right atrium, it would be desirable and advantageous to provide a device for assisting the flow of blood from the coronary sinus back to the right atrium.

Accordingly, it is desirable and advantageous to provide a device for draining the coronary sinus to enhance the operation of a heart. The present invention is designed to facilitate venous drainage of blood from the coronary sinus to the right atrium or the right ventricle of the heart. In particular, the present invention assists in coronary venous drainage by employing a pair of catheters, a control device having a pump and a sensor pair that provides signals to the control device for the control device to operate the pump. The present invention also accomplishes venous drainage.

SUMMARY OF THE INVENTION

In one form of the present invention, a device for draining a coronary sinus comprises a first catheter having a distal end, a proximal end, and a passage there through, the distal end adapted to be placed in a coronary sinus, a second catheter having a distal end, a proximal end, and a passage there through, the distal end adapted to be placed in a right side of a heart, and a control system for receiving signals indicative of a coronary sinus needing to be drained of blood, the control system comprising a pump for pumping blood from a coronary sinus through the first catheter to the second catheter into a right side of a heart. The catheters may be coated within and without with an agent to prevent coagulation or clotting.

In another form of the present invention, a device for draining a coronary sinus comprises a first catheter having a distal end, a proximal end, a first passage, a second passage, a inflatable cuff positioned near the distal end and in communication with the second passage, the distal end adapted to be placed in a coronary sinus, a second catheter having a distal end, a proximal end, and a passage there through, the distal end adapted to be placed in a right side of a heart, and a control system for receiving signals indicative of a coronary sinus needing to be drained of blood, the control system comprising a first pump for pumping blood from a coronary sinus through the first catheter to the second catheter into a right side of a heart, and a second pump connected to the second passage of the first catheter for inflating or deflating the inflatable cuff.

In yet another form of the present invention, a method of assisting drainage of blood from a coronary sinus is disclosed that comprises the steps of inserting a first catheter into a coronary sinus, inserting a second catheter into a right side of a heart, determining when blood needs to be drained from a coronary sinus to a right side of a heart, and pumping blood from a coronary sinus through the first catheter through the second catheter into a right side of a heart when it is determined that blood needs to be drained.

Accordingly, it will be recognized that an object of the present invention is to provide a device for effectively moving blood from the coronary sinus of the heart to be discharged into the right atrium or the right ventricle of the heart.

A further object of the present invention is to provide a device for draining the coronary sinus which is of simple construction and design and which can be easily employed with highly reliable results.

Another object of the present invention is to provide a device for draining the coronary sinus that can be easily inserted into the coronary sinus and the right atrium or the right ventricle.

A further object of the present invention is to provide a device for draining the coronary sinus that is durable during use by a patient.

It is a further object of the present invention is to provide a device for draining the coronary sinus that is capable of improving cardiac output, reduce heart failure, and ameliorate muscle damage due to a heart attack.

A still further object of the present invention is to provide a device for draining the coronary sinus that reduces possible trauma to the heart.

Another object of the present invention is to provide a device for draining the coronary sinus having a pair of catheters with the catheters being coated with an anticoagulant drug.

These and other objects and advantages of the present invention will become apparent after considering the following detailed specification in conjunction with the accompanying drawings, wherein:

BRIEF DESCRIPTION OF THE DRAWINGS

FIG. 4 is an enlarged partial view of an inflatable cuff portion of the device for draining the coronary sinus;

FIG. 5 is an enlarged partial view of the inflatable cuff portion positioned at the distal end of one of the catheters of the device for draining the coronary sinus;

FIG. 6 is a partial view of the first and second catheters of the device for draining the coronary sinus;

FIG. 9 is a second preferred embodiment of a device for draining a coronary sinus constructed according to the present invention;

FIG. 10 is a partial cross-sectional view of a distal end of a catheter employed in the second preferred embodiment;

FIG. 11 is a partial cross-sectional view of another distal end of a catheter employed in the second preferred embodiment; and FIG. 12 is a partial cross-sectional view of yet another distal end of a catheter employed in the second preferred embodiment.

DETAILED DESCRIPTION OF THE PREFERRED EMBODIMENTS

Figures 1, 2, 3:
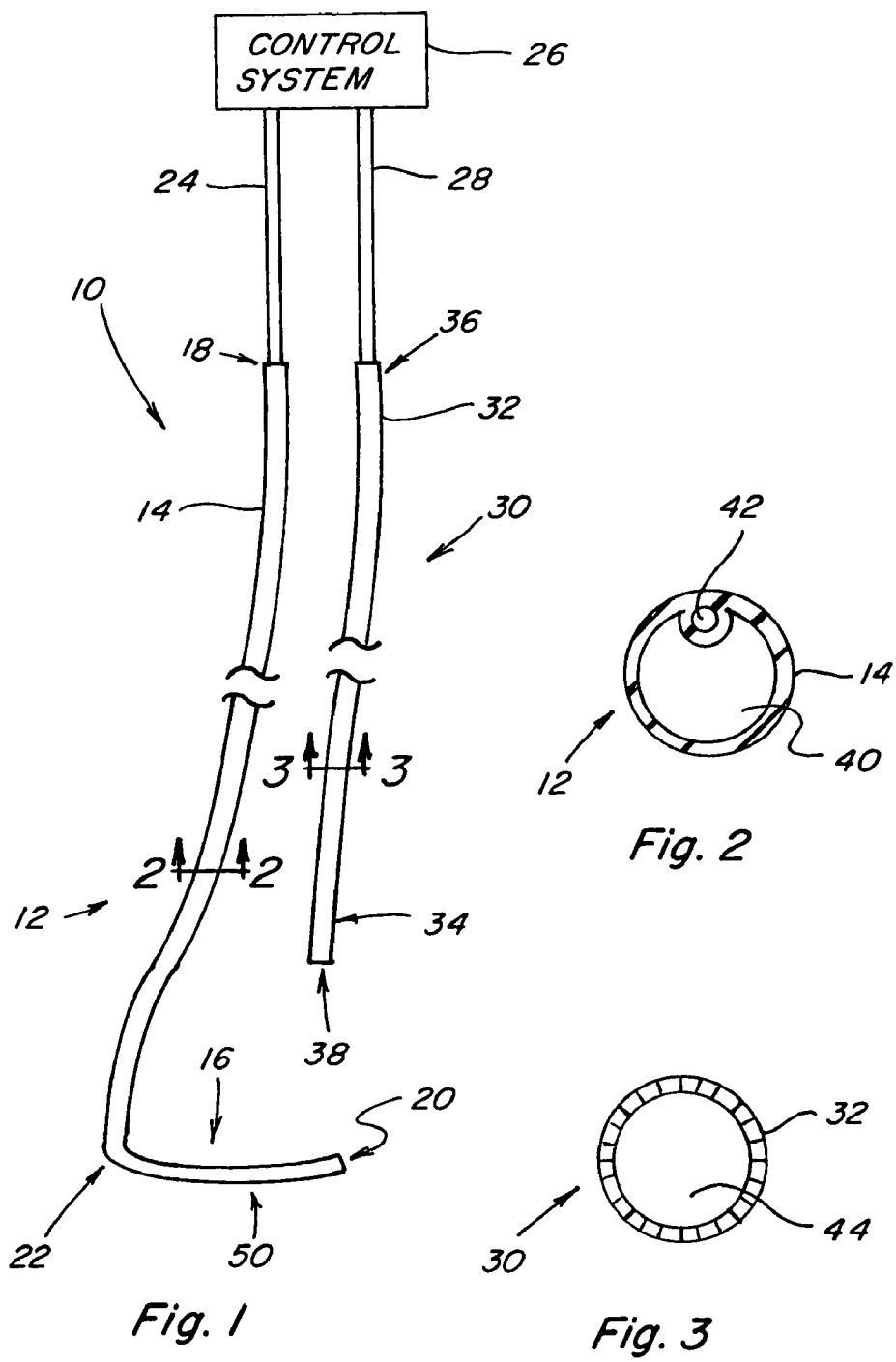
FIG. 1 is a perspective and block diagram view of a preferred embodiment of a device for draining a coronary sinus constructed according to the present invention.
FIG. 2 is an enlarged cross section view taken along the plane of line 2-2 of FIG. 1 of the device for draining the coronary sinus.
FIG. 3 is an enlarged cross-sectional view taken along the plane of line 3-3 of FIG. 1 of the device for draining the coronary sinus.

Referring now to the drawings, wherein like numbers refer to like items, number 10 identifies a preferred embodiment of a device for draining the coronary sinus constructed according to the present invention. With reference now to FIG. 1, the device 10 is shown comprising a first catheter 12 having a catheter shaft 14 configured for retrograde deployment within a patient through an internal jugular vein or a subclavian vein. The catheter 12 has a distal end 16 and a proximal end 18. The distal end 16 has a bore 20 with a diameter from 0.5 cm to 2.5 cm. The distal end 16 may be preshaped in the form of an L-shape 22 to facilitate placement of the catheter 12 in a patient's heart or coronary sinus and to improve the stability of the catheter 12. The catheter shaft 14 may be reinforced by use of braided or coiled wire to add to the strength of the catheter 12. The catheter 12 is adapted to being placed or inserted into the coronary sinus for draining blood from the coronary sinus.

The proximal end 18 of the catheter 12 is connected to a tube 24 with the tube 24 being connected to a control system 26. The control system 26 has another tubing 28 that is connected to a second catheter 30. The catheter 30 has a catheter shaft 32 that is configured for deployment or insertion into a patient through an internal jugular vein or a subclavian vein to the right atrium of the heart. The catheter 30 has a distal end 34 and a proximal end 36. The distal end 34 has a bore 38 having a diameter from 0.5 cm to 2.5 cm. The proximal end 36 is connected to the tubing 28. The second catheter 30 is inserted into the right atrium of the heart. The control system 26, as will be described in detail further herein, is used to drain blood from the coronary sinus to the right atrium. Blood is removed from the coronary sinus through the first catheter 12 and the tubing 24 and pumped into the right atrium via the tubing 28 and the second catheter 30.

The first catheter shaft 14 and the second catheter shaft 32 may be formed of a flexible thermoplastic material, a thermoplastic elastomer, or a thermoset elastomer. The catheter shafts 14 and 32 may also be fabricated separately by known extrusion methods and joined together end-to-end, for example by heat welding or by adhesive bonding. Alternatively, the catheter shafts 14 and 32 may be fabricated by dipping or by composite construction techniques and joined together. The catheter shafts 14 and 32 may also be fabricated or formed as a unitary construction. Suitable materials for the first catheter shaft 14 and the second catheter shaft 32 include, but are not limited to, polyvinylchloride, polyurethane, polyethylene, polypropylene, polyamides, nylons, polyesters, silicone, latex, and alloys or copolymers thereof, as well as braided, coiled, or counterwound wire or filament reinforced composites.

It is also contemplated and possible that the first and second catheter shafts 14 and 32 be coated in an interior surface and an exterior surface with an anticoagulant drug such as Argatroban or heparin to prevent coagulation or clotting. Other examples of an anticoagulant drug that may coat the shafts 14 and 32 are a thrombin inhibitor such as hirudin, hirudin and its isopeptides, hirulog, D-phenlalanyl-L-poly-L-arginyl chloromethyl ketone, low molecular weight heparin, forskolin, vapiprost, prostacyclin and its analogues, dextran, D-phe-pro-arg-chloromethyl ketone, angipepetin, dipyndamole, glycoprolein IIb/IIa platelet membrane receptor, or another antithrombogenic agent or mixtures thereof. The anticoagulant drug may be deposited on and in the shafts 14 and 32 in any known manner such as by vapor deposition or plasma deposition.

With reference now to FIG. 2, an enlarged cross-sectional view of the first catheter 12 is illustrated. The catheter 12 has a pair of internal lumens 40 and 42 within the catheter shaft 14. The first internal lumen 40 is adapted for draining blood there through from the coronary sinus to the control system 26. The second internal lumen 42 is used to inflate a balloon, as will be explained further herein. The second internal lumen 42 is also connected to the control system 26. Both the interior and exterior surfaces of the lumens 40 and 42 may be coated with an anticoagulant drug to prevent coagulation or clotting.

FIG. 3 depicts an enlarged cross-sectional view of the second catheter 30. The second catheter 30 has the catheter shaft 32 surrounding an internal lumen 44. The internal lumen 44 is connected to the control system 26 and is used to return or pump blood into the right side of the heart through either the right atrium or the right ventricle. The interior surface of the lumen 44 and the exterior surface of the catheter 30 may be coated with an anticoagulant drug.

An inflatable cuff 50 that is mounted or positioned near the distal end 16 of first catheter 12 is shown in FIG. 4. The inflatable cuff 50 is an expandable or inflatable balloon 52 that may be formed from suitable materials such as flexible polymers and elastomers, polyvinylchloride, polyurethane, polyethylene, polypropylene, polyamides, polyesters, latex, and silicone. The inflatable cuff 50 has a deflated state wherein the diameter of the cuff 50 is about the outside diameter of the catheter shaft 14 and an inflated state wherein the diameter of the cuff 50 is greater than the outside diameter of the catheter shaft 14. The second internal lumen 42 has a bore 54 through which air or other inflation material or fluid may flow to inflate the cuff 50. The cuff 50 may be deflated by removal of the air by the control system 26. The balloon 52 may have an inflated diameter of 1.5 cm to 5.0 cm. However, other diameters may be used or selected depending upon the size of the heart to be treated or assisted. It is also possible and contemplated to position the balloon 52 of the inflatable cuff 50 at or on the distal end 16 of first catheter 12. This particular embodiment is depicted in FIG. 5.

FIG. 6 illustrates the first and the second catheters 12 and 30 in further detail. The first catheter 12 has the catheter shaft 14 stopping at the proximal end 18 with the tubing 24 extending out from the proximal end 18. The tubing 24 surrounds the first internal lumen 40 and the second internal lumen 42. The first internal lumen 40 terminates at a connector 60 that is adapted to be connected to a pump (not shown) that is used to drain blood from the coronary sinus. The second internal lumen 42 also terminates at a connector 62 that is to be connected to another pump (also not shown) that is used to inflate or deflate the inflatable cuff 50. The connectors 60 and 62 may be different sizes or shapes to be able to correctly orientate the connectors 60 and 62 to a suitable pump. The second catheter 30 has the catheter shaft 32 stopping at the proximal end 36 with the tubing 28 extending out from the proximal end 36. The tubing 28 surrounds the internal lumen 44 with the lumen 44 terminating at a connector 64. The connector 64 is adapted to be connected to the pump that the first internal lumen 40 is connected. In this manner, blood drained out of the coronary sinus through the first internal lumen will be sent to the lumen 44 and out of the catheter 30 into the right side of the heart.

Figure 7:
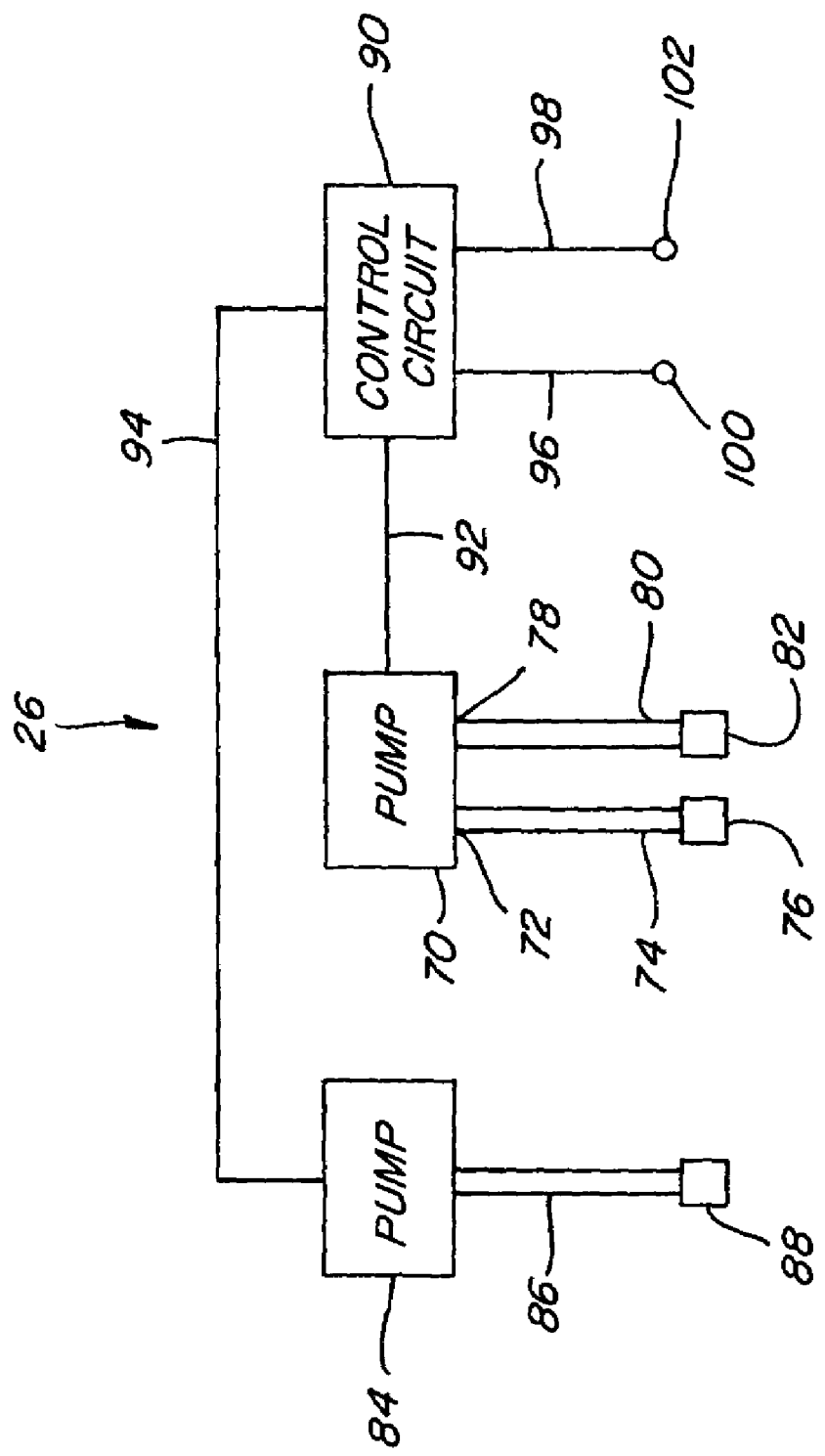
FIG. 7 is a block diagram view of the control system for the device for draining the coronary sinus.

With reference now to FIG. 7, a block diagram of the control system 26 for controlling operation of the device 10 is shown. The control system 26 has a first pump 70 that is used to pump or drain blood from the coronary sinus through the first internal lumen 40 and out the lumen 44 into the right side of the heart. The pump 70 has an inlet 72 that is connected to a tube 74 having an end connector 76. The end connector 76 is constructed to mate with the connector 60 of the first internal lumen 40. The pump 70 also has an outlet 78 that is connected to a tube 80 that has an end connector 82. The end connector 82 is configured to mate with the connector 64 of the second catheter 30. An inflation pump 84 is also part of the control system 26. The inflation pump 84 has a tube 86 to connected to the pump 84. The tube 86 also terminates at a connector 88. The connector 88 is adapted to fit with the connector 62 of the second internal lumen 42. The inflation pump 84 is used to inflate or deflate the inflatable cuff 50.

A control circuit 90 is electrically connected to the pump 70 via a wire 92. The control circuit 90 is capable of controlling operation of the pump 70 by the wire 92. The inflation pump 84 is also connected to the control circuit 90 by a wire 94. Signals sent over the wire 94 from the control circuit 90 control operation of the inflation pump 84. The control circuit 90 also has a pair of leads 96 and 98 connected to a pair of sensor pads 100 and 102. The pads 100 and 102 may be positioned on a patient's chest to be able to obtain information for determining a pumping cycle for the heart. Further, the pads 100 and 102 may be positioned by having one of the leads on the housing and another lead located on the exterior surface of one or both of the catheters. The control circuit 90 may include circuitry capable of determining the PQRST signal of the heart as obtained by an EKG. An input signal is provided via the leads 96 and 98 to the control circuit 90 indicating when the systolic and diastolic periods of a patient's heart begin. This signal can be taken from the Q wave of an electrocardiograph and stopping at the T wave. The pump 70 may begin draining blood from the coronary sinus into the right atrium or the right ventricle starting at the presence of the Q wave and stopping when the T wave is encountered. Further, if a patient has a pacemaker, these signals may be obtained directly from the pacemaker. If for some reason the Q and T wave signals are not available or are too weak then other signals for determining the timing of the control circuit 90 may be obtained from arterial or ventricular pressure. Also, if a patient needs to be paced, leads for pacing can be placed on the exterior surfaces of the catheters 12 and 30 for pacing purposes.

Figure 8:
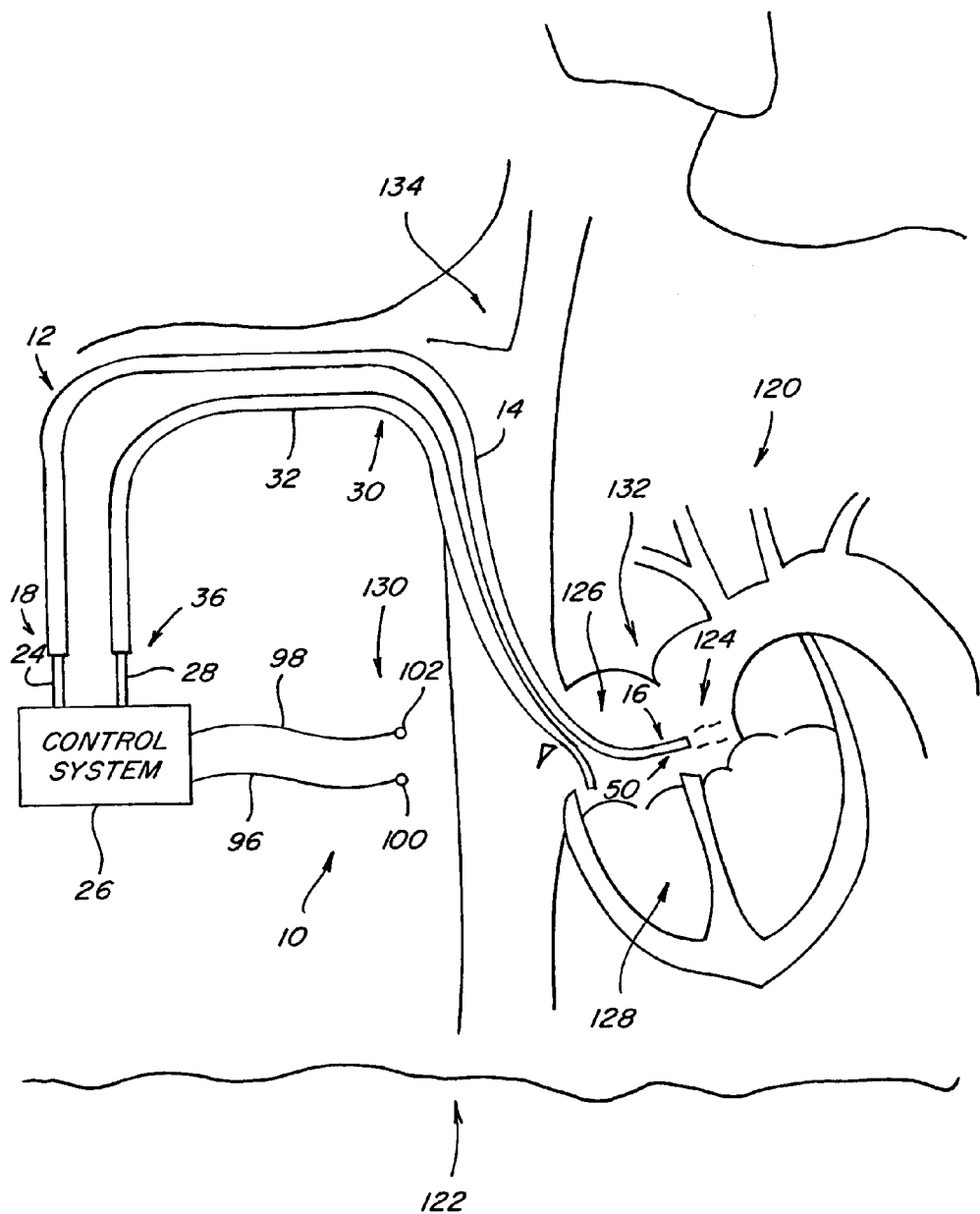
FIG. 8 is a schematic illustration of the device for draining the coronary sinus inserted into a patient.

Referring now to FIG. 8, a schematic illustration of the device 10 for draining the coronary sinus is shown inserted into a heart 120 of a patient 122. The proximal end 16 of the first catheter 12 is inserted into a coronary sinus 124 of the heart 120. The first catheter 12 is connected to the pump 70 (not shown) in the control system 26. The catheter 12 is capable of draining blood from the coronary sinus 124 to the pump 70 and out the pump 70 through the second catheter 30 into a right atrium 126 of the heart 120. Although not shown, the catheter 30 is also capable of pumping blood into a right ventricle 128 of the heart 120 when the catheter 30 is inserted into the right ventricle 128. The pump 84 (not shown) within the control system 26 is able to inflate or deflate the inflatable cuff 50 of the first catheter 12. The inflatable cuff 50 is shown in the deflated state in FIG. 8. The pads 100 and 102 are shown being placed on a chest 130 of the patient 122. The pads 100 and 102 are connected to the control system 26 via the wires 96 and 98, respectively. The control system 26 is capable of receiving signals from the pads 100 and 102 that are representative of the heartbeat or the PQRST signal generated by an EKG. The control system 26 is able to determine when to begin pumping of the pump 70 and to stop the pump 70. In this manner, blood is drained or pumped from the coronary sinus 124 to the right atrium 126 or to the right ventricle 128 or to a right side 132 of the heart 120.

As can be appreciated, the device 10 may include one or more markers to enhance imaging of the device 10 or the catheters 12 and 30 for positioning the device 10 in the coronary sinus 124 and the right atrium 126 or the right ventricle 128. The catheters 12 and 30 may include radiopaque markers and/or sonoreflective markers to navigate the catheters 12 and 30 using fluoroscopy or ultrasound. Examples of a radiopaque marker may be a ring of dense radiopaque metal such as gold, platinum, tungsten or alloys thereof. Further, the catheters 12 and 30 may be inserted into the patient 122 through an internal jugular vein 134. Although not shown, the catheters 12 and 30 may be inserted into the patient 122 through a subclavian vein. As is know, contrast solution may also be injected into the patient 122 to facilitate positioning of the catheters 12 and 30 in the coronary sinus 124 and the right atrium 126 or the right ventricle 128.

With particular reference now to FIG. 9, a second preferred embodiment of a device for draining a coronary sinus 200 is shown. The device 200 comprises a first catheter 202 having a catheter shaft 204 configured for retrograde deployment within a patient through an internal jugular vein or a subclavian vein. The catheter 202 has a distal end 206 and a proximal end 208. The distal end 206 has a bore or an opening 210 having a diameter from 0.5 cm to 2.5 cm. The distal end 206 may be preshaped in the form of an L-shape 212 to facilitate placement of the catheter 202 in a patient's heart or coronary sinus and to improve the stability of the catheter 202. The catheter shaft 204 may be reinforced by use of braided or coiled wire to add to the strength of the catheter 202. The catheter 202 is adapted to being placed or inserted into the coronary sinus for draining blood from the coronary sinus.

The proximal end 208 of the catheter 202 is connected to a control system 214. The control system 214 is connected to a second catheter 216. The catheter 216 has a catheter shaft 218 that is configured for deployment or insertion into a patient through an internal jugular vein or a subclavian vein into the right side of the heart into either the right atrium or the right ventricle. The catheter 216 has a distal end 220 and a proximal end 222 that is connected to the control system 214. The distal end 220 has a bore or an opening 224 having a diameter from 0.5 cm to 2.5 cm. As previously indicated, the second catheter 216 may be inserted into the right atrium or the right ventricle of the heart. The control system 214 is used to drain blood through the first catheter 202 from the coronary sinus through the second catheter 216 into the right atrium or the right ventricle. As previously discussed with reference to the device 10, the device 200 may include one or more markers to enhance imaging of the device 200 or the catheters 202 and 216 for positioning the device 200 in the coronary sinus and the right side of the heart.

The first catheter shaft 202 and the second catheter shaft 216 may be formed of a flexible thermoplastic material, a thermoplastic elastomer, or a thermoset elastomer. The catheter shafts 202 and 216 may be fabricated by dipping or by composite construction techniques and joined together. Alternatively, the catheter shafts 202 and 216 may also be fabricated separately by known extrusion methods and joined together end-to-end, for example by heat welding or by adhesive bonding. The catheter shafts 202 and 216 may also be fabricated or formed as a unitary construction. Suitable materials for the first catheter shaft 202 and the second catheter shaft 216 include, but are not limited to, polyvinylchloride, polyurethane, polyethylene, polypropylene, polyamides, nylons, polyesters, silicone, latex, and alloys or copolymers thereof, as well as braided, coiled, or counterwound wire or filament reinforced composites. As previously indicated, the first catheter 202 and second catheter 216 may be coated on an interior surface and an exterior surface with an anticoagulant drug such as Argatroban or heparin or other anticoagulant drugs. Other examples of an anticoagulant drug that may coat the shafts 202 and 216 are a thrombin inhibitor such as hirudin, hirudin and its isopeptides, hirulog, D-phenlalanyl-L-poly-L-arginyl chloromethyl ketone, low molecular weight heparin, forskolin, vapiprost, prostacyclin and its analogues, dextran, D-phepro-arg-chloromethyl ketone, angipepetin, dipyndamole, glycoprolein IIb/IIIa platelet membrane receptor, or another antithrombogenic agent or mixtures thereof. The anticoagulant drug may be deposited on and in the shafts 202 and 216 in any known manner such as by vapor deposition or plasma deposition.

A distinction between the device 200 and the device 10 is that there is no inflatable cuff 50 in the device 200 and there is no second internal lumen or passage 42 in the catheter 202. Further, the control system 214 is modified to remove the pump 84 that is used to inflate the cuff 50. Also, although not shown, the control system 214 may include circuitry capable of determining the PQRST signal of the heart in order to determine appropriate times when to drain blood through the catheter 202 and out of the catheter 216. For example, a signal indicative of the beginning of the Q wave and the ending of the T wave may be used to start and stop the device 200.

FIG. 10 depicts another embodiment of the distal end 206 of the catheter 202 of the device 200. In this particular embodiment the distal end 206 has a solid round shaped terminal protuberance 230. The terminal protuberance 230 may take on different shapes such as a solid tear shape 232, as shown in FIG. 11, or a solid elliptical shape 234, as shown in FIG. 12.

From all that has been said, it will be clear that there has thus been shown and described herein a device for draining the coronary sinus which fulfills the various objects and advantages sought therefor. It will become apparent to those skilled in the art, however, that many changes, modifications, variations, and other uses and applications of the subject device for draining the coronary sinus are possible and contemplated. All changes, modifications, variations, and other uses and applications which do not depart from the spirit and scope of the invention are deemed to be covered by the invention, which is limited only by the claims which follow.

What is claimed is:

1. A method of assisting drainage of blood from a coronary sinus comprising the steps of inserting a first catheter into a coronary sinus, inserting a second catheter into a right side of a heart, determining when blood needs to be drained from a coronary sinus to said right side of said heart, and pumping blood from a coronary sinus via the first catheter, through the second catheters and into said right side of said heart when it is determined that blood needs to be drained.

2. The method of claim 1 further comprising the step of inflating an inflatable cuff positioned at a distal end of the first catheter.

3. The method of claim 1 further comprising the step of deploying the first and second catheters through an interior jugular vein prior to inserting the first catheter into said said coronary sinus and prior to inserting the second catheter into said right side of said heart.

4. The method of claim 1 wherein the determining step further comprises the step of monitoring signals indicative of systole and diastole of said heart and starting and stopping pumping of blood from said coronary sinus to a right side of said heart depending upon the monitoring signals indicative of systole and diastole of said heart.

5. The method of claim 1 wherein said second catheter is inserted into an atrium on said right side of said heart.

6. The method of claim 1 wherein said second catheter is inserted into a ventricle on said right side of said heart.

7. The method of claim 1 further comprising the step of deploying the first and second catheters through a subclavian vein prior to inserting the first catheter into said coronary sinus and prior to inserting the second catheter into said right side of said heart.

* * * * *

UNITED STATES PATENT AND TRADEMARK OFFICE
CERTIFICATE OF CORRECTION

PATENT NO.       : 7,347,810 B2
APPLICATION NO.  : 10/956973
DATED            : March 25, 2008
INVENTOR(S)      : Thomas A. Stamos It is certified that error appears in the above-identified patent and that said Letters Patent is hereby corrected as shown below:

Column 4, fourth paragraph, line 47, after the word glycoprolein, it reads "IIb/IIa"; it should read -- IIb/IIIa --.

Signed and Sealed this

Fifth Day of August, 2008

JON W. DUDAS
*Director of the United States Patent and Trademark Office*